United States Patent
Lim et al.

(10) Patent No.: US 8,535,361 B2
(45) Date of Patent: Sep. 17, 2013

(54) METHOD AND PORTABLE SYSTEM FOR NON-INVASIVE, IN-VIVO BLOOD IRRADIATION LIGHT THERAPY

(76) Inventors: Teng Lew Lim, Toronto (CA); Kam Ming Yip, Selangor (MY); Teng Howe Lim, Kuala Lumpur (MY)

( * ) Notice: Subject to any disclaimer, the term of this patent is extended or adjusted under 35 U.S.C. 154(b) by 351 days.

(21) Appl. No.: 12/802,866

(22) Filed: Jun. 16, 2010

(65) Prior Publication Data
US 2010/0324632 A1 Dec. 23, 2010

Related U.S. Application Data

(60) Provisional application No. 61/213,558, filed on Jun. 19, 2009.

(51) Int. Cl.
*A61N 5/06* (2006.01)
*A61B 19/00* (2006.01)
(52) U.S. Cl.
USPC .................. 607/89; 607/88; 607/92; 128/898
(58) Field of Classification Search
USPC ...................................... 607/88–94; 128/898
See application file for complete search history.

(56) References Cited

U.S. PATENT DOCUMENTS

| 4,576,168 A * | 3/1986 | Jalowayski | 606/198 |
| 2007/0219600 A1* | 9/2007 | Gertner et al. | 607/88 |
| 2009/0227997 A1* | 9/2009 | Wang et al. | 606/10 |

* cited by examiner

*Primary Examiner* — Dawayne A Pinkney
(74) *Attorney, Agent, or Firm* — David Prashker, Esq.

(57) ABSTRACT

The present invention is a non-invasive apparatus, system, and method for performing irradiation light therapy upon blood circulating within the nostrils of a living mammalian subject. The merit and medical value of the invention resides in its ability to achieve a reversal of red blood cell aggregation in-vivo without invading the tissues or organs of the living subject—a clinical result which leads to lower blood viscosity and improved blood circulation. In this manner, the invention provides the living mammalian subject with an enhanced immunity from diseases, a reduced vulnerability to hypertension, and a reduced risk of a cardiovascular incident. Furthermore, by altering the wavelengths transmitted by the light generating unit(s) and controlling the light energy dosage, the method and system can also fine-tuned further as intervention for various diseases.

19 Claims, 13 Drawing Sheets

Fig. 6
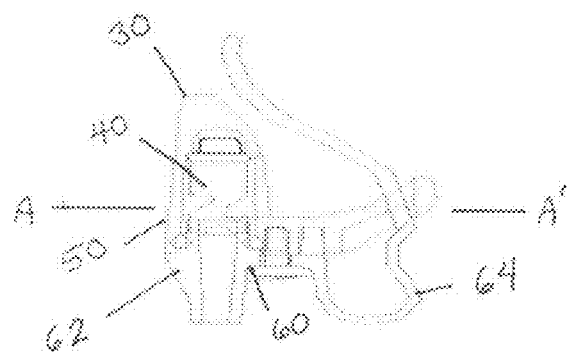
Fig. 6A
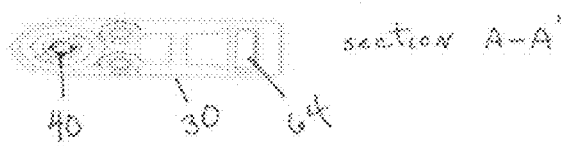
Fig. 6B
Fig. 7
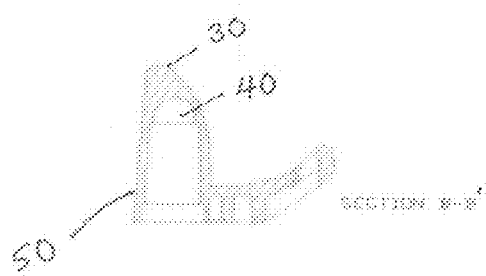
Fig. 7A
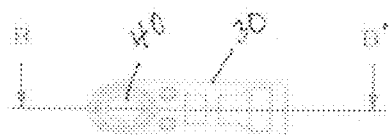
Fig. 7B

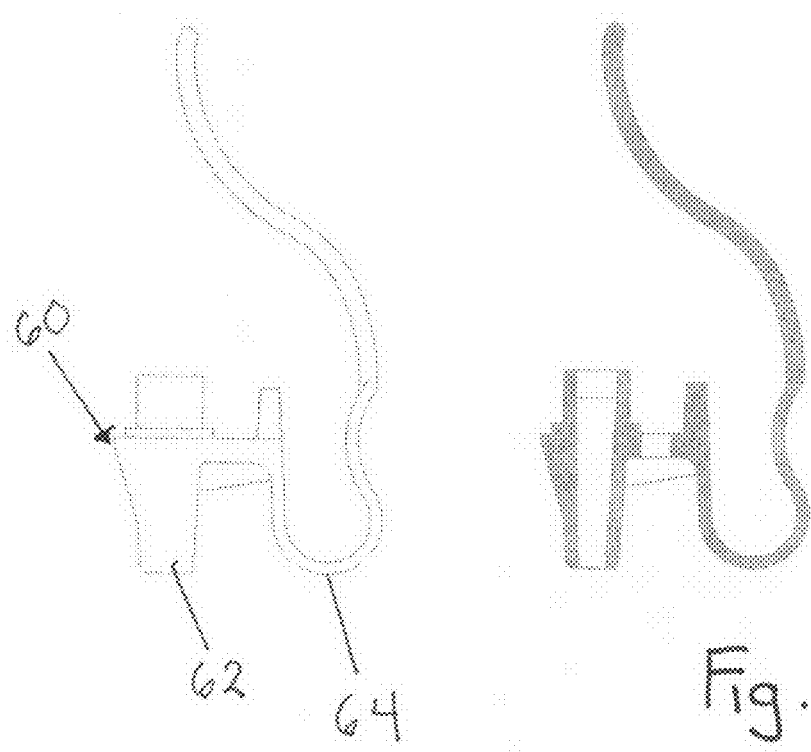

Fig. 9
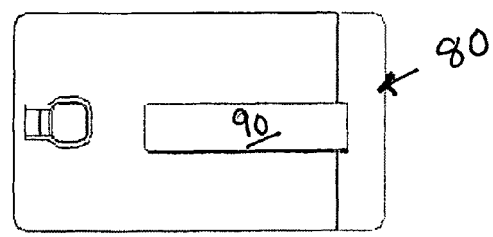
Fig. 9A
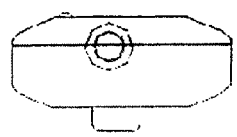
Fig. 9B
Fig. 9C
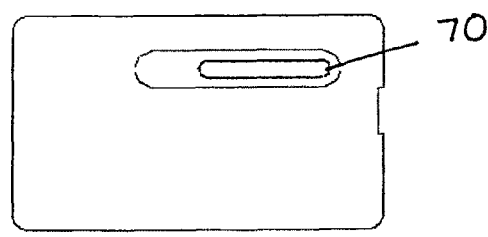
Fig. 9D

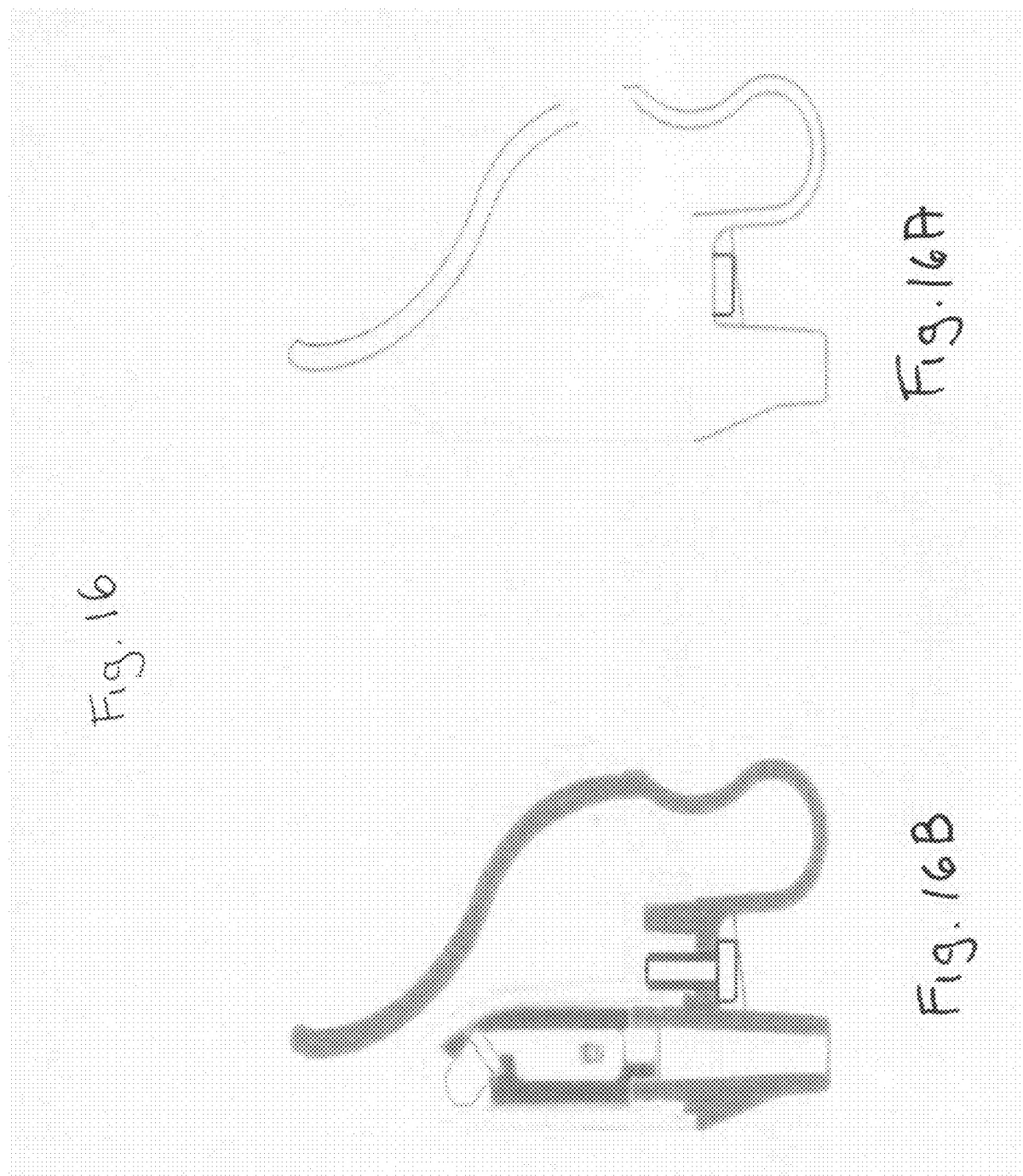

METHOD AND PORTABLE SYSTEM FOR NON-INVASIVE, IN-VIVO BLOOD IRRADIATION LIGHT THERAPY

CROSS-REFERENCE

The invention was first filed as U.S. Provisional Patent Application Ser. No. 61/213,558 on Jun. 19, 2009. The legal priority and benefits of this first filing are expressly claimed herein.

FIELD OF THE INVENTION

The invention is concerned with in vivo irradiation light therapy of the blood system. More particularly, the invention is directed to a portable and convenient apparatus, system and methodology by which the user can self-administer light therapy without any need for medical or technical supervision. The apparatus is configured for portability; provides for the insertion of an applicator with a light source into the nasal cavity to achieve the desired therapeutic effect; and incorporates an optical design and user interface configuration to achieve a high level of efficacy.

BACKGROUND OF THE INVENTION

Although blood irradiation therapy is not commonly known nor frequently used today within the United States as a mode of medical treatment, this therapeutic procedure is well established and often employed in both Eastern and Western European countries, all of Scandinavia, and throughout Asia. Over its history of medical use, low level laser light therapy has been called by different and alternative names, such as "photobiostimulation", "cold laser therapy", and "laser biostimulation".

Origins and History

It is believed that the first report of blood irradiation therapy was published by Russian scientists in 1981 [Mishalkin, E., editor (1981), "Application of direct laser irradiation in experimental and clinical heart surgery (in Russian)", Novosibirsk: Nauka]. The Mishalkin reported a technique that involved inserting a cannula that contained a plastic laser catheter into a vein in the forearm of a human patient and feeding the low intensity laser light into the blood stream through the cannula. This mode of treatment was developed for the treatment of cardiovascular diseases, in which both the microcirculation and the rheological properties of blood were improved by the treatment.

The initial Mishalkin publication was then supported by later studies; and positive findings based on this method of intravenous blood irradiation with low level light therapy (or "LLLT") have been consistently reported [see for example, Boev et al. (1997), "The impact of He—Ne-laser therapy on the antioxidant system in patients with stable insertion angina and postinfarkt cardiosclerosis" Klin-Med-Mosk, 75(12): 30-3; and Khotiantsev et al (1996), "Laser blood irradiation effect on physiological characteristics of acute coronary syndrome patients", Proceedings of SPIE 2929: 132-137].

Later published studies also demonstrated that blood rheology can be improved not only with low level laser light, but also with green laser light wavelengths [Mi et al (2004), "A comparative study of 632.8 and 532 nm laser irradiation on some rheological factors in human blood in vitro", Journal of Photochemistry and Photobiology B., 74:1: 7-12; and blue laser light [Gasparyan, L (2003), "Laser irradiation of the blood", Laser Partner Clinixperience:58; and online at www-.laserpartner.org/lasp/web/en/2003/0058.htm].

Still later reported studies also have suggested that it does not matter if the light energy is coherent (i.e., laser light); rather, but whether the light energy is of the right wavelength and is delivered at the correct dosage. For example, incoherent red from an LED is expected to perform as well as laser light to produce low-power laser clinical effects; and the primary difference between laser light and LED light is that the laser's coherent beam produces "speckles" of relatively high power density which can cause local heating of inhomogeneous tissues" [see for example, Karu, T. I. (1998), "The Science of Low Power Laser Therapy", Gordon and Breach Scientific Publications, London].

Conventionally Used Therapeutic Procedures

Several different techniques are currently known:
1. Clinically, the traditional manner of intravenously administering light therapy is still performed today as: (i) intravenously inserting a catheter into a blood vessel in the forearm (or other limb); and then (ii) delivering low level laser light through the lumen of the catheter and thereby irradiate the patient's blood as it circulates.

Medically, intravenous laser blood irradiation has been shown to be therapeutically functional and effective for multiple effects including: (1) Stimulating the immune response of the living subject; (2) activating erythrogenesis; (3) improving deformability of erythrocyte membranes; (4) causing anti-hypoxic activity on living tissues; (5) initiating a general antitoxic influence on the living body against different pathological processes; and (6) having biostimulative, analgetic, antiallergic, immunocorrective, antitoxic, vasodilative, antiarrythmic, antibacterial, antihypoxic, spasmolytic, anti-inflammatory and other properties" [see for example, Gasparyan, L. (2003), "Laser Irradiation of the blood", Laser Partner Clinixperience:58; Mester et al (1967), "Effect of laser on hair growth of mice", Kiserl Orvostud 19:628-631; M H Knisely, "Intravascular erythrocyte aggregation (blood sludge)", in: Handbook of Physiology, Section 2: Circulation, Vol. III, Am. Physiol. Soc., Bethesda, Md., 1965, pp 2249-2292; G. Mchedlishvili, L. Gobejishvili and N. Beritashvili, "Effect of intensified red blood cell aggregability on arterial pressure and mesenteric microcirculation," Microvascular Research, 45 (1993), pp 233-242; G Ciuffetti, G Schillaci, R Lombardini, M Pirro, G vaudo, M Mannarino, "Plasma viscosity in isolated systolic hypertension: The role of pulse pressure", American journal of hypertension, 2005, vol. 18, pp 1005-1008; D E Brooks, R G Greig, 3 Janzen, "Mechanisms of erythrocyte aggregation", Erythrocyte Mechanics and Blood Flow (Eds. G R Cokelet, H J Meiselman, D E Brooks) A. R. Liss. New York, 1980, pp. 119-140; S Chien, K M Jan, "Ultrastructural basis of the mechanism of rouleaux formation", Microvascular Research 5, 1973, pp 155-166].

Also, a number of published studies present the view that major medical benefits are obtainable through LLLT blood irradiation—many of these benefits stemming from the disaggregation of red blood cells, a reduced blood viscosity, and improved blood rheology [see for example Stroev et al (1990), "The treatment of diabetic angiopathies by endovascular low intensity laser irradiation", Probl-Endokrinol-Mosk, 36(6): 23-5]. Consequently, LLLT as a therapeutic technique has been deemed to be desirable and useful for treating many different diseases, disorders, and pathologies.

In addition, several health and cosmetic benefits have resulted from the use of LLLT. Thus today, LLLT is commonly used to stimulate hair growth, for pain management, and for skin rejuvenation. In addition, more recent NASA-supported studies have reported that incoherent red light from light emitting diodes provide beneficial effects such as wound healing [Whelan et al, (December 2001) "Effect of NASA light emitting diode irradiation on wound healing", Journal of Clinical Laser Medicine & Surgery 19(6): 305-314].

2. Another and alternative method for blood irradiation is the procedure known as "Ultraviolet Blood Irradiation". This procedure was often used for the treatment of disease in the U.S. in the 1940's and 1950's, but has fallen out of favor since that time with the introduction of the far more effective prophylactic vaccines. Nevertheless, this technique remains an alternative mode of therapy.

The classic manner for performing Ultraviolet Blood Irradiation is a closed loop system involving withdrawing blood intravenously from the patient and returning it after passing the blood through an ultraviolet (UV) light irradiation unit. Its proponents believe that this medical procedure is able to treat a long and varied number of diseases particularly those that relate to bacterial infections; and more detailed information can be obtained by visiting websites such as http://en.wikipedia.org/wiki/Ultraviolet_blood_irradiation. The focus on bacterial infections are somewhat different from low level laser and red light therapy irradiation of the blood which improves blood rheology. Nevertheless, this technique is an invasive and inconvenient method of blood irradiation, with the patient needing to be hooked up to the UV irradiation equipment at a medical center.

3. There is one conventionally known medical procedure that is non-invasive as such. This procedure involves administering laser light transcutaneously over the skin at specifically targeted large blood vessels, such as those large veins located beneath the human forearm. However, when using this transcutaneous irradiation technique, it has been estimated that this method takes 20 times more power to achieve the same benefit when compared with the direct intravenous irradiation method [Gasparyan, L. (2003), "Laser Irradiation of the blood", Laser Partner Clinixperience:58]. Moreover, the resulting therapeutic effects of such transcutaneous treatment have been found to be far less reliable or predictable.

The Long-Standing Difficulties and Continuing Problems of LLLT

The reported therapeutic efficacies of LLLT have been achieved via the invasive method of intravenous blood irradiation using light of preselected wavelengths. However, in order to benefit from intravenous blood irradiation, each and every patient must make frequent and regular visits to a specially trained physician and a facility suitable for such invasive treatment. Furthermore, each intravenous light therapy session will take about 20-60 minutes to perform; and the expected span of treatment will typically require from 3 to about 10 sessions. This is unfortunately an uncomfortable and inconvenient treatment regimen at best.

There is another obstacle as well for LLLT. This invasive mode of blood irradiation treatment has not been approved by the U.S. Food and Drugs Administration (FDA); and hence is not lawfully licensed for medical use in the U.S. and in several other countries (e.g., Canada, Mexico and Australia), except for licensed experimental research purposes via a pre-approved FDA New Drug/Device Application.

Overview

For these reasons, the development of a non-invasive and convenient mode and manner of performing therapeutic blood irradiation remains a long awaited and sought after goal. Moreover, the development of an apparatus and system that not only eliminates, or at least minimizes these inconveniences; but also provides a treatment method that is reliable in performance, and is reliable in its effects, and is as efficacious as the traditional invasive procedures would encourage more widespread usage of light therapy irradiation of the blood. Accordingly, such a development would be recognized and appreciated as a major advance in the technical field by physicians and patients alike.

SUMMARY OF THE INVENTION

The present invention has several aspects:

A first aspect provides an apparatus for performing non-invasive irradiation light therapy within a nasal cavity of a living mammalian subject, said non-invasive apparatus comprising:

a portable hollow casing having fixed dimensions, a sized internal spatial volume, and an external surface configuration suitable for in-vivo insertion into the nasal cavity space of a nostril without causing substantial impairment to the subject's ability to breathe, said portable casing being comprised of (i) a light transmitting material which forms at least a portion of the external surface for said casing, (ii) at least one light generating unit disposed within said internal spatial volume of said casing and which is capable of generating light energy of at least one preselected wavelength on-demand;

means for at will in-vivo placement of a light transmitting external surface of said casing and said light generating unit within a human nostril at a position adjacent to the internal lining and internal blood vasculature of a subject's nasal cavity;

a portable and replenishable power source of on-demand direct electrical current;

a portable controller assembly including (α) a receiving circuit for receipt of such direct electrical current as is transferred to said controller from said power source, (β) a central processing unit for controlling and directing the flow of such direct electrical current as is received, and (γ) a conveying circuit for conveying direct electrical current from said controller assembly to said light generating unit;

at least one connector in electrical communication with said source of electrical current for on-demand transfer of direct electrical current to said controller assembly; and at least one connector in electrical communication with said controller assembly and said light generating unit for on-demand conveyance of direct electrical current from said controller assembly.

A second aspect of the invention is a non-invasive system for performing irradiation light therapy within a nasal cavity of a living mammalian subject, said system comprising:

a configured irradiation lens including a portable hollow casing having fixed dimensions, a sized internal spatial volume, and an external surface configuration suitable for in-vivo insertion into the nasal cavity space of a nostril without causing substantial impairment to the subject's ability to breathe, said portable casing being comprised of (i) a light transmitting material which forms at least a portion of the external surface for said casing, (ii) at least one light generating unit disposed within said internal spatial volume of said casing and which is capable of emitting light energy on-demand of at least one preselected wavelength;

applicator means adapted for support of said configured irradiation lens and for at will placement of a light transmitting external surface of said configured irradiation lens within a human nostril at a position adjacent to the internal lining and internal blood vasculature of a subject's nasal cavity;

a portable controller assembly including
(α) a portable and replenishable power source of on-demand direct electrical current,
(β) a central processing unit for controlling and directing the flow of such direct electrical current, and
(γ) at least one connector in electrical communication with said configured irradiation lens for on-demand conveyance of direct electrical current from said controller assembly to said light generating unit.

A third aspect of the invention provides a method for performing non-invasive irradiation light therapy within a nasal cavity of a living mammalian subject, said non-invasive therapy method comprising the steps of:

obtaining an apparatus comprised of
a configured irradiation lens including
a portable hollow casing having fixed dimensions, a sized internal spatial volume, and an external surface configuration suitable for in-vivo insertion into the nasal cavity space of a nostril without causing substantial impairment to the subject's ability to breathe, said portable casing being comprised of
(i) a light transmitting material which forms at least a portion of the external surface for said casing,
(ii) at least one light generating unit disposed within said internal spatial volume of said casing and which is capable of emitting light energy on-demand of at least one preselected wavelength, portable means for supporting said configured irradiation lens and for at will placement of a light transmitting external surface of said configured irradiation lens within a nostril at a position adjacent to the internal lining and internal blood vasculature of a subject's nasal cavity, a portable controller assembly including
(α) a portable and replenishable power source of on-demand direct electrical current,
(β) a central processing unit for controlling and directing the flow of such direct electrical current, and
(γ) at least one connector in electrical communication with said configured irradiation lens for on-demand conveyance of direct electrical current from said controller assembly to said light generating unit;

placing a transparent external surface of said configured irradiation lens within a nostril at a position adjacent to the internal lining and internal blood vasculature of a subject's nasal cavity; and causing said light generating unit of said positioned configured irradiation lens to generate light energy of at least one preselected wavelength upon the internal lining and internal blood vasculature of a subject's nasal cavity for a predetermined amount of time.

BRIEF DESCRIPTION OF THE FIGURES

The present invention may be easily understood and more readily appreciated when taken in conjunction with the Drawing, in which:

FIGS. 6A and 6B are illustrations showing a perspective view and a cross-sectional view of the applicator in the preferred apparatus as seen in FIG. 3;

FIGS. 7A and 7b are illustrations showing a perspective view and a cross-sectional view of the irradiation lens in the preferred apparatus as seen in FIG. 3;

FIGS. 8A and 8b are illustrations showing a perspective view and a cross-sectional view of the applicator in the preferred apparatus as seen in FIG. 5A;

FIGS. 9A-9D are illustrations showing top, side, and bottom perspective views of the process controller assembly in the preferred apparatus as seen in FIG. 3;

FIGS. 16A and 16B are illustrations showing a perspective view and a cross-sectional view of the applicator inserted into a nostril of a living human subject as seen in FIG. 13.

DETAILED DESCRIPTION OF THE INVENTION

Figure 1:
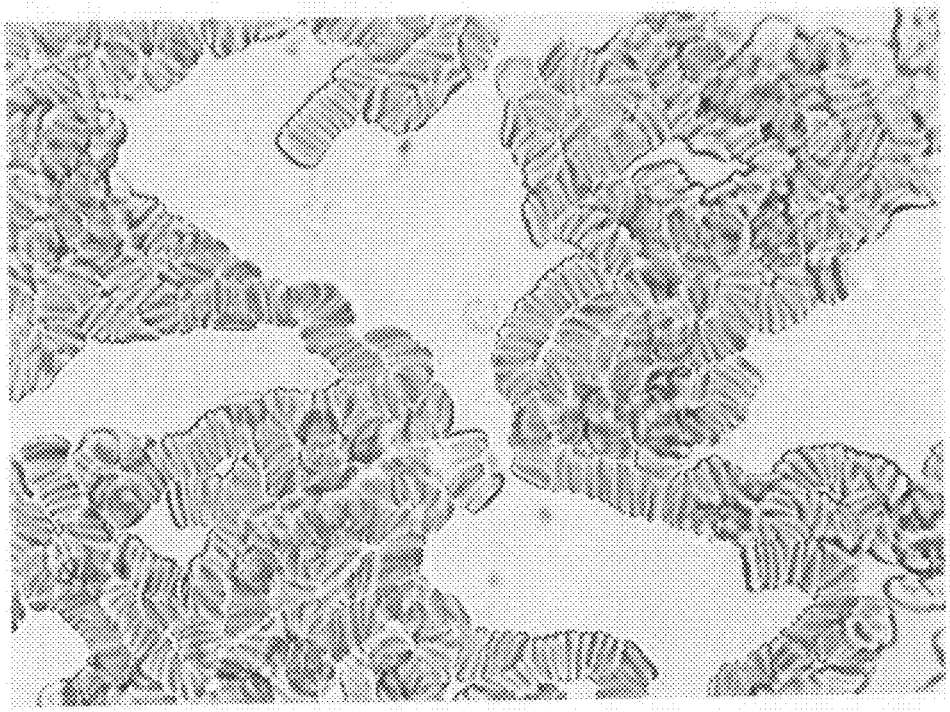
FIG. 1 is a microphotograph showing multiple red blood cell clusters in the circulating blood of an unhealthy human subject.

The present invention is a non-invasive apparatus, system, and method for performing irradiation light therapy upon blood circulating in-vivo within the nostrils of a living mammalian subject. The performance and medical value of the invention resides in its ability to achieve a reversal of red blood cell aggregation in-vivo without invading the tissues or organs of the living subject—a clinical result which leads to a lower blood viscosity and an improved blood circulation. By performing in this non-invasive manner, the invention provides the living mammalian subject with an enhanced immunity from diseases, a reduced vulnerability to hypertension, and a reduced risk of a cardiovascular incident. Furthermore, by altering the wavelengths of light transmitted by the light generating unit(s) and controlling the light energy dosage, the invention can also markedly reduce the number and variety of pathogens then present in the living body.

When using the present invention, light energy is therapeutically delivered through the nasal cavity to irradiate the vascular capillaries located directly underneath the walls forming the interior of the nasal cavity. The therapeutic benefits of such nasal irradiation light therapy are then spread throughout the whole body via the blood circulation system.

Advantages and Benefits

The instant invention provides a number of desirable advantages and unexpected benefits for the prospective user. These include the following:

- The apparatus is medically non-invasive in each and every embodiment and instance of use.
- The apparatus is dedicated to and designed for at will attachment to and detachment from the nose.
- The apparatus is compact, and collectively is smaller in overall size than a cigarette pack.
- The apparatus is extremely light in weight and is easily transported by hand over any distance.
- The apparatus is comfortable and easy to use.
- The apparatus is to be self-administered routinely and repetitiously by the patient for therapeutic treatment, and does not require any assistance by a medical technician.
- The apparatus can alternatively employ either a laser or a light emitting diode as a light generating unit.
- The apparatus can generate light energy waves and particles at any desired medically effective wavelength(s) chosen from the visible, near-infrared, and infrared light ranges.
- The apparatus causes no significant electromagnetic or other interference with other medical devices, and thus is suitable for use by persons having an implanted pacemaker or defibrillator.
- Preferred embodiments of the apparatus deploy a low level laser diode with 655 nm generated light. Such apparatus is regulated in power to only about 5-10 mW and preferably uses a 1.5 volt battery as a source of direct electric current. The power and battery requirements are specific to the light source.
- Preferred embodiments of the apparatus are typically regulated to 5 mW of laser light power (energy/sec of light measured from the laser light unit). If another source of light energy is used, such as a light emitting diode (or "LED"), then the power will be regulated to control that source of light energy.
- Preferred embodiments of the apparatus are simple to use by any person in that one merely uses his fingers to clip the applicator onto a nostril and presses the "power on" button.
- Preferred embodiments of the apparatus include both a timer and an automatic shut-off switch which self-engages after 25 minutes use time. The preferred 25 minute treatment duration is medically relevant; and the actual treatment time may vary depending on the choice of light source.
- Preferred embodiments of the apparatus are highly resistant to accidental injury, and are able to withstand a drop of 5 feet without incurring any damage.
- Preferred embodiments of the apparatus employ a process controller assembly which ensures that the light energy delivered to the nasal cavity is consistent. If the battery is unable to sustain a consistent power to drive the circuit to power the light source, the process controller assembly will give a warning and will switche off the device.

I. The Underlying Premises of the Invention

Initially, it is useful to describe briefly what are the underlying medical premises and clinical support for the subject matter as a whole which is the present invention. The factual summaries given below provide the true context and perspectives for properly understanding and appreciating the merits of the invention.

Normal Disaggregated and Unhealthy Aggregated Red Blood Cells

A blood profile analysis will clearly reveal what a person's state of health actually is. A blood sample from an unhealthy subject shows that his red blood cells (RBCs) are joined together and form an aggregate; and the presence of such RBC aggregates creates a marked resistance to flow or "high viscosity" for the circulating blood in that individual. Under a microscope, the blood sample of an unhealthy subject would typically appear as shown by FIG. 1, where aggregated RBCs form irregular clusters or masses of cells.

Figure 2:
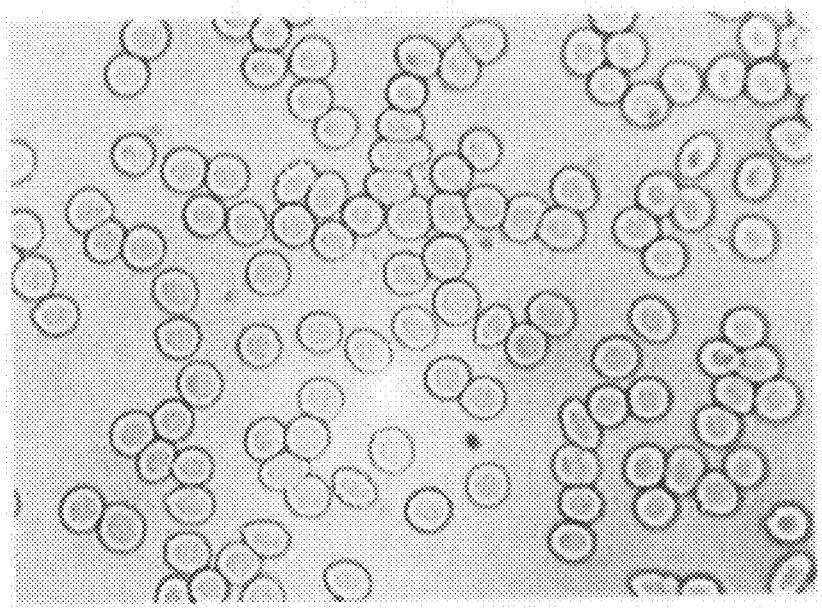
FIG. 2 is a microphotograph showing separate and individual red blood cells in the circulating blood of a healthy human subject.

In comparison, if the same person were in a healthy medical condition, his blood sample would look entirely different in its morphology, and appear as shown by FIG. 2 in a non-aggregate form as separate RBCs.

Visually, it is clear that one primary morphological difference between the two blood samples is how the red blood cells (RBCs or erythrocytes) are seen to be aggregated clusters in FIG. 1, but exist as disaggregated and separate cells in FIG. 2. It is also noteworthy that, albeit not visibly demonstrated by FIG. 2, the non-aggregated RBC sample is markedly less viscous in comparison to the blood aggregates of FIG. 1.

Functions of Blood and why it should be Free of RBC Aggregations

Normal circulating blood—i.e., blood containing non-aggregated RBCs—performs many important life functions in the mammalian body. Among these are the following:

- Blood provides a supply of oxygen to living tissues via the hemoglobin internally carried by RBCs.
- Blood provides a supply of nutrients such as glucose, amino acids and fatty acids. These nutrients are dissolved in the blood or are bound to plasma.
- Blood acts to remove waste products such as carbon dioxide, urea and lactic acid.
- Blood performs diverse immunological functions, including the circulation of multiple kinds of white blood cells as well as the detection and binding of foreign material by antibodies.
- Blood provides the cascade of proteins needed for blood clotting or coagulation as part of the body's self-repair mechanisms.
- Blood provides the entities for messenger functions, including the transport of hormones and the chemical signaling of tissue damage.
- Blood serves to regulate body pH via blood acidity.
- Blood regulates the core body temperature.
- Blood performs many hydraulic (fluid mechanical) functions.

Medical Significance of RBC Aggregates in the Blood

For these reasons, when the RBCs in the circulating blood aggregate into masses and form irregular clusters of cells, at least some functional roles of blood become severely compromised. Medically in these situations, the RBC aggregation is due to the presence of molecular proteins, such as fibrinogen. Fibrinogen is sensitive to inflammation and helps with the blood clotting function; and thus is an important factor in RBC aggregation. Therefore, the presence of RBC masses and aggregates in the circulating blood is a clinical marker and indicator that the body is now in an unhealthy physiological state.

Equally important, and without regard to any specified causes, there is little question that RBC massing and aggregation result in the circulation of blood being less efficient in moving RBCs into the various tissues and organs of the living body. For all of these reasons therefore, it is deemed to be both medically desirable and clinically therapeutic if such RBC aggregates as appear in the circulating blood could be made to dissociate and disaggregate into separated and individual red blood cells.

The Nostrils and the Nasal Cavity

Typically for a healthy person, blood in many parts of the body takes less than one minute's time to circulate completely throughout the body. In most anatomic areas of the body, however, the blood vascular system lies either shallowly or deeply in the connective tissues existing below the dermal and epidermal layers of the skin. In particular, there are very few anatomic locations which allow the vascular capillary beds to lie near the skin surface; and even in these superficial locales, the vascular capillary beds near the skin are protected by being enclosed within the interior of naturally occurring body cavities which typically conceal the capillaries from direct exposure to the ambient air environment.

One such superficial anatomic locale and body orifice is the mammalian nose, as exemplified best by the human nostrils. Anatomically, the human nose is comprised of two distinct nostrils, leading to a common internal nasal cavity which is formed and defined by thin mucous membrane walls. Situated just beneath and adjacent to the thin mucous membrane walls forming the shaped surfaces of the nasal cavity space is a rich vascular capillary bed; and these capillaries are specifically designed by nature to allow a rapid passage of fluid matter (mucous, lymph, serum proteins) from the circulating blood through the vascular capillary wall and into the tissues and the ambient air environment of the nasal cavity space [see for example, Chien et al (1989), "Nasal Systemic Drug Delivery", Chapter 1: Anatomy and Physiology of the Nose, Dekker, New York: 1-26].

It is noted also that the vascular capillary walls lying adjacent to the nasal cavity are particularly thin and sensitive, thus making them highly receptive to any kind of biostimulation. Furthermore, the quantity of blood which flows into this nasal capillary bed area is quite large; and the rate of blood flow here is routinely higher per unit area of tissue in comparison to the rate of blood flow into other anatomic locales such as the brain, or the liver, or the muscles.

II. A Preferred Embodiment of the Present Invention

Initially, it is desirable to present here one preferred example which can be prepared as a commercially salable embodiment and is presently considered to be the best mode of the invention. This preferred embodiment and best mode of the non-invasive apparatus is shown by FIGS. 3-10 and FIGS. 13-16 respectively as an unified and ready to use medical device.

As seen therein, the non-invasive apparatus 10 provides an applicator 20, a structural vehicle of convenience, which holds and supports a configured irradiation lens 50 which is small in size and is purposefully shaped to allow its insertion into a nasal cavity space without causing meaningful impairment to the subject's ability to breathe. The configured irradiation lens 50 itself, however, is formed as a resulting combination and integration of two separate structural entities: a portable transparent and partially hollow casing 30; and at least one discrete light generating unit 40, which is entirely housed and contained within the interior spatial volume of the hollow casing 30.

The configured irradiation lens 50 is formed at least in part of a light transmitting material; and serves to direct most of the generated light in the desired direction—i.e., towards to the nostril wall of the nasal cavity. In the embodiment shown by FIGS. 3-5, a low level laser—i.e., a laser in which the energy level is so low that it does not raise the tissue temperature—is used as the preferred light generating unit 40. In other alternative embodiments of the apparatus, a LED light source can be used. In either instance, the generated light will become pointed and aimed in the desired direction (see FIGS. 7 and 14).

In the preferred format, the applicator 20 is a single cooperative entity which provides and includes a support base 60 for the configured irradiation lens 50; and is collectively structured as a discrete cradle section 62 and a contoured nose clip or fitting 64 fashioned for easy at will attachment to and detachment from the exterior surface of the human nostril. The nose clip 64—apart from serving physically as contoured friction fitting by which to hold the configured irradiation lens 50 in proper position within the nostril—is preferably composed of a white or opaque material which contributes to its service as a light barrier and reflector, and which acts to redirect some stray light passing through the tissue wall of the nostril back towards the interior of the nasal cavity wall.

Figure 3:
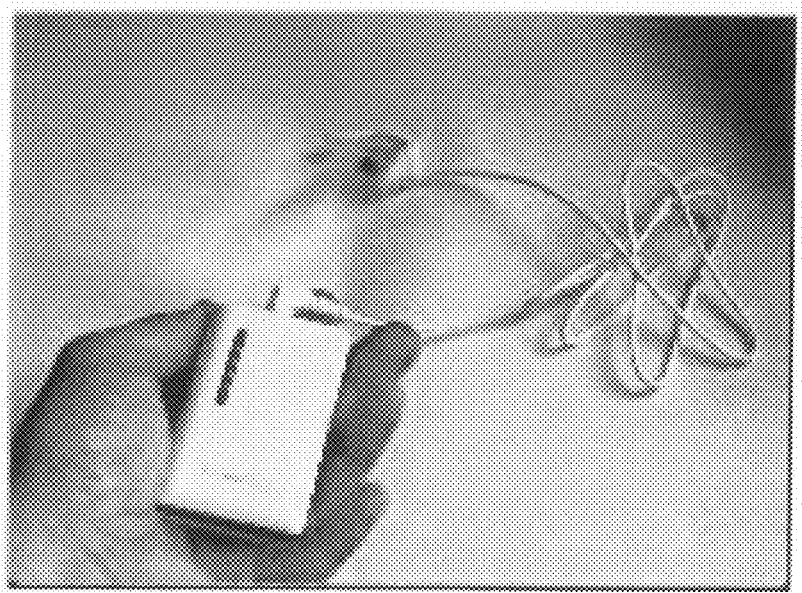
FIG. 3 is a photograph showing a preferred embodiment of the apparatus comprising the present invention.
Figure 4:
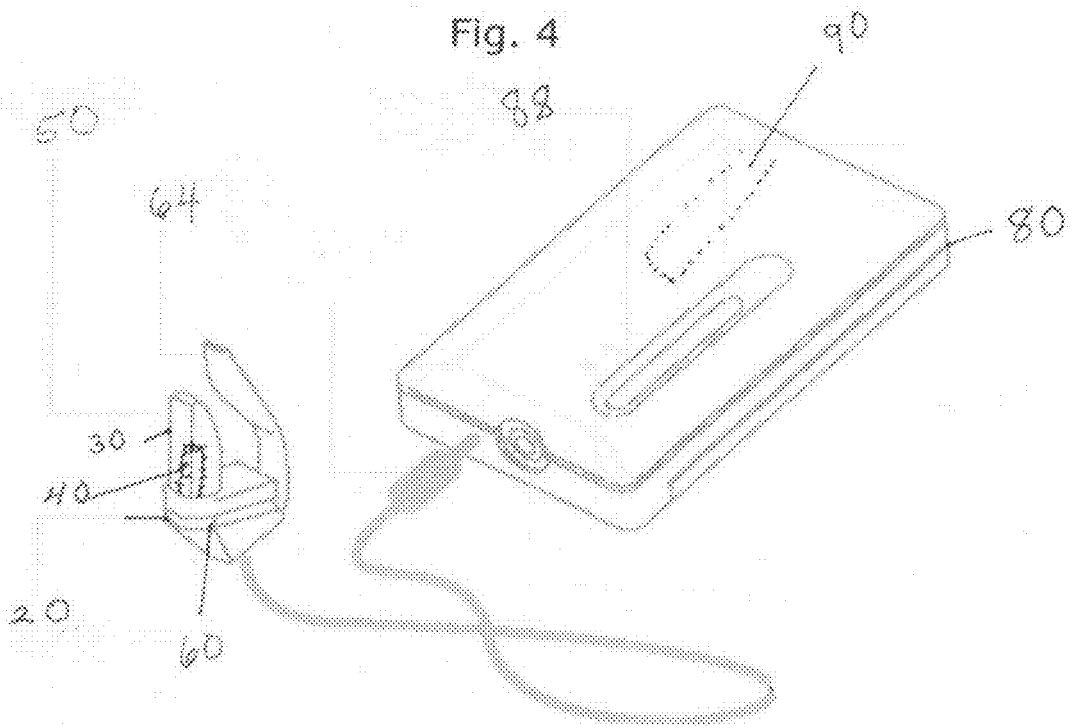
FIG. 4 is an illustration showing the individual component parts of the preferred apparatus as seen in FIG. 3.

In addition, as appears in FIGS. 3-4 respectively, the configured irradiation lens 50 is in electrical communication via a cable and jack module connector 70 with a process controller assembly 80—a control and power supply construct which is compact, lightweight and sufficiently portable to be carried by hand or to fit inside a shirt pocket. In this preferred format, the process controller assembly 80 includes a portable and replenishable source of on-demand direct electrical current and is able to convey carefully regulated dosages of electric power on-demand to the light generating unit(s) contained within with the hollow casing for light irradiation therapy. In this instance, the process and power controller assembly 80 also includes and provides an automatic timer and power switch 88. The controller automatically shuts off the electric current conveyed to the light generating unit(s) after the passing of a pre-chosen amount of time.

The Configured Irradiation Lens

Architecturally, the preferred configured irradiation lens 50 appears as a substantially "L" shaped construct, as shown in detail by FIGS. 6 and 7 respectively. The configured irradiation lens 50 as such, however, is always formed by and is the result of combining and integrating two other separate and essential structural entities: a portable hollow casing 30, formed in least in part of a light transmitting material, and which serves at least in part as a reflective lens that reflects light in a desired direction; and at least one discrete light generating unit 40, which is entirely housed and contained within the interior spatial volume of the hollow casing 30. Together the discrete light generating unit 40 and the portable hollow casing 30 collectively form the configured irradiation lens 50, a construct able to emit and direct light energy of at least one predetermined wavelength on-demand.

Thus, in this illustrated embodiment and use context, the configured irradiation lens 50 as a whole includes the entire "L" shaped construction. It is critical, therefore to understand and appreciate the meaning and effect of this "L" shaped construction; and attention is therefore directed to the views provided by FIGS. 6A-6B and FIGS. 7A-7B respectively.

As shown therein, although the hollow casing 30 is formed as a lens and includes the entire "L" shaped structure, the light generating unit 40 is typically placed into and contained by only the vertical or upright volumetric portion 32 of the "L" shaped casing. Consequently via this arrangement, the horizontal or axial portion 34 of the hollow casing 30 is typically devoid of any internal contents; and exists merely for physical support by the cradle section 62 of the supporting base 60 in the applicator 20. Also, via this positioning arrangement, it is only the vertical or upright volumetric portion 32 of the "L" shaped casing which must be formed of a light-transmitting or transparent material. In contrast, the horizontal or axial portion 34 of the hollow casing 30 may be formed of any resilient material, transparent or not.

An Optionally Present Micro-Lens

Figure 13:
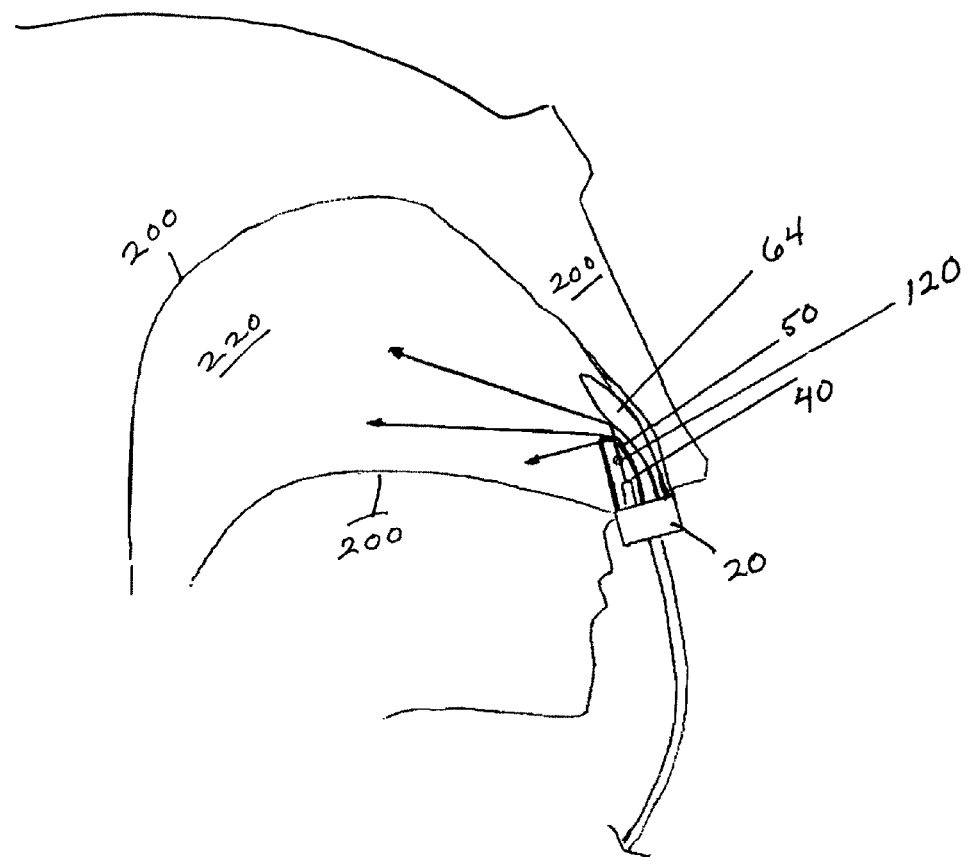
FIG. 13 is a cross-sectional view of the applicator properly inserted into a nostril of a living human subject.
Figure 14:
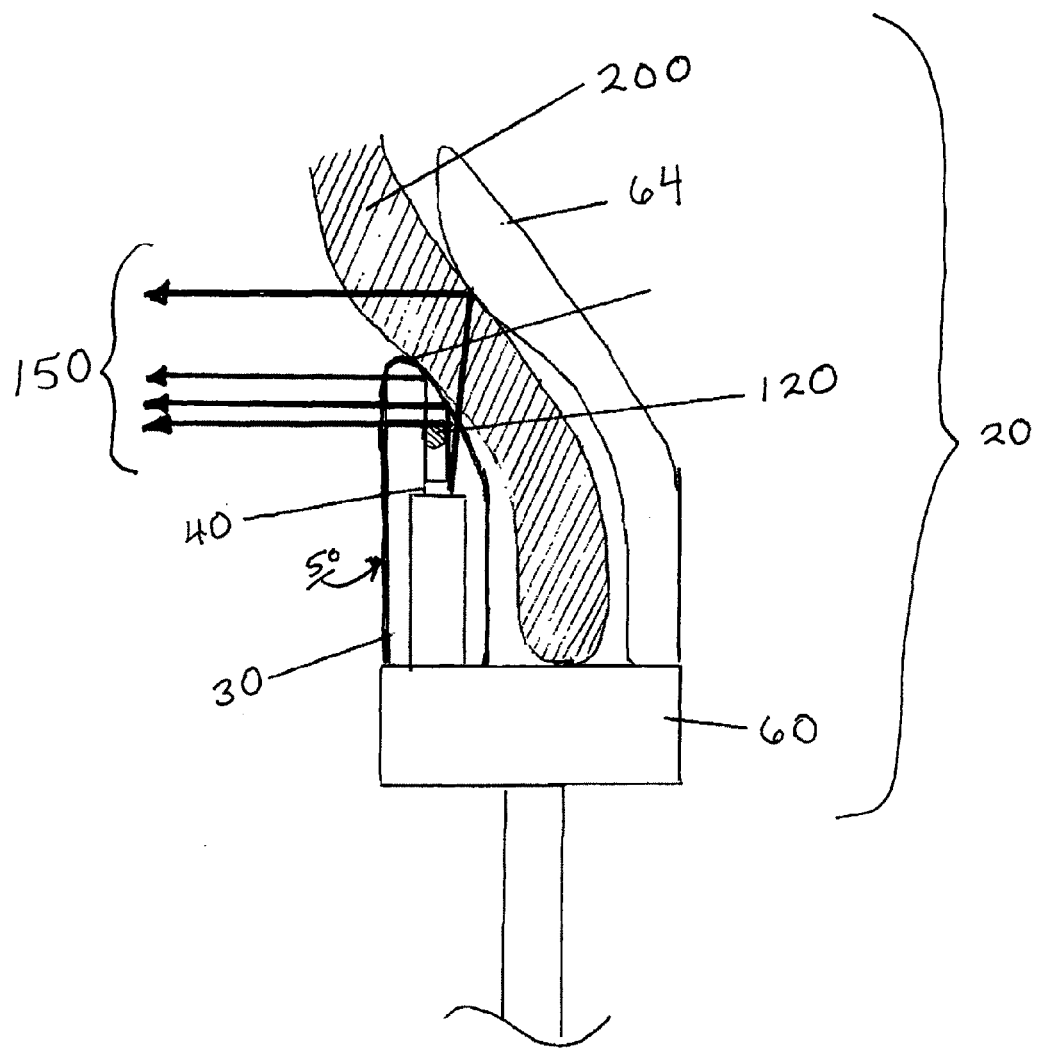
FIG. 14 is a more detailed cross-sectional view of the applicator inserted into a nostril of a living human subject as seen in FIG. 13.

In the preferred embodiments of the apparatus utilizing a low level laser as the light generating unit (as illustrated by FIGS. 13 and 14 respectively), there is an optionally present spherical micro-lens 120 disposed next to the emission end or tip of the laser light generating unit 40 within the hollow casing 30. The placement of this optionally present spherical micro-lens 120 is shown best by FIGS. 14 and 15.

It will be noted and appreciated, however, that the inclusion and use of a spherical micro-lens is most applicable only to the laser diode light generating unit design, and is not necessarily a structural feature for other embodiments of the apparatus using LEDs as the light generating source. In addition, if and when a micro-lens is present, the overall configuration of the micro-lens may be varied for different embodiments. Clearly, it is not necessary for the micro-lens to be spherical in shape; instead, its configuration can alternatively be a reverse tear drop shape, an oval or oblong shape, or any other rotund configuration which redirects light particles towards a desired direction.

Accordingly, the inclusion of a micro-lens 120 is an optional, but highly desirable, structural feature of the configured irradiation lens 50; and when present, is placed and aligned adjacent to the emitted light in order to control light dispersion and direct light particles towards the deeper regions of the nasal cavity where the rich vascular capillary beds are located. The emitted light becomes largely deflected and aimed towards the internal section of the nasal cavity by reflection against the curved tip of the casing 30 together with the optional micro-lens 120.

The combined effect of the embedded micro-lens 120, the configured tip of the casing 30, and the light reflecting nose clip 64 effectively capture and redirect most of the generated light into the interior of the nasal cavity. In this way, the amount of electrical energy needed to achieve therapeutic efficacy is kept to a minimum, and achieves the goal of the apparatus being small, portable and convenient to use.

The Applicator

The applicator 20 is a purposeful grouping together of parts designed to form a non-essential, but desirable, hand held article which can be manipulated with the fingers and is suitable for at will attachment to and detachment from a nostril. In particular, as shown by FIGS. 6A-6B and 8A-8B, it is the combination of the configured irradiation lens 50 together with the support base 60 and the nose clip 64 which collectively form and constitute the applicator 20; and as such, the applicator 20 is merely a construction of personal convenience for the patient.

It will be therefore appreciated that, it is the configured irradiation lens 50 which is the truly essential component—a distinct entity which is desirably held within and is supported by a cradle 62 in a supporting base 60. The cradle 62 holds and aligns the configured irradiation lens 50 for easy and rapid insertion into the nasal cavity space.

Figure 5A:
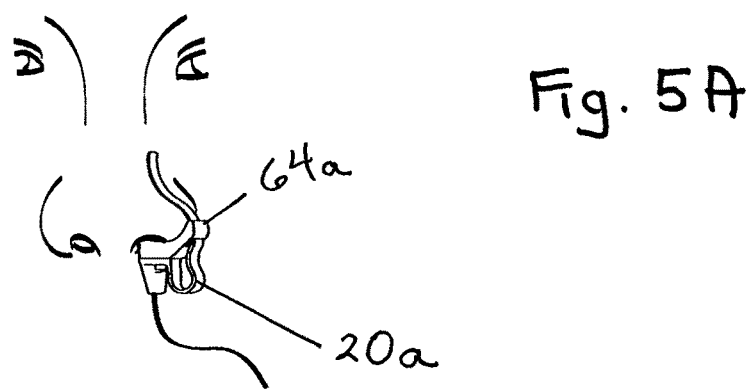
FIGS. 5A and 5B are illustrations showing alternative structural formats for the applicator in the preferred apparatus as seen in FIG. 3.
Figure 5B:
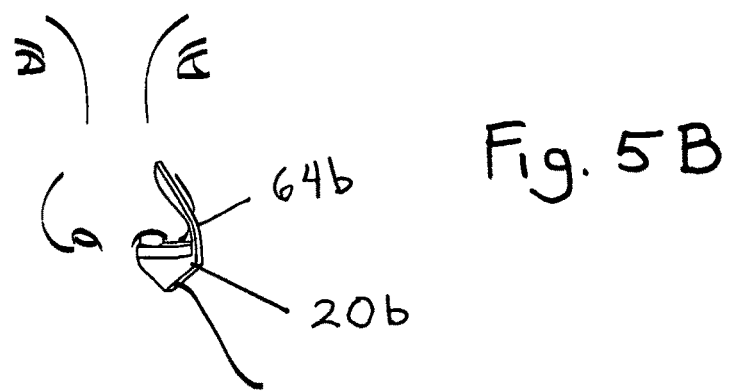

Note also that the styled nose clip 64 of the applicator 20 is a structural material arm and outward extension of the supporting base 60. Typically, the nose clip 64 is formed of a white or opaque material which is both flexible and resilient. Two different structural formats of the nose clip 64a and 64b are shown by FIGS. 5A and 5B respectively.

In its preferred embodiments, the nose clip serves two different purposes and functions: First, it is employed for direct pressure contact against and fitted frictional engagement with the exterior surface of the human nose. This engagement maintains the inserted irradiation lens in proper position within the nasal cavity space. Second, the white or opaque material of the nose clip will reduce leakage of some light particles and reflect stray light particles back into the interior tissues of the nostril. The nose clip 64 performs both of these intended functions as a merged part of the applicator 20.

For these reasons, the applicator 20 as a distinct entity—and in contrast to the configured irradiation lens 50—is merely article of convenience which facilitates usage of the apparatus 10 as whole. The applicator 20 is easy to manipulate using the fingers of the human hand; and thus is a very desirable vehicle for the proper positioning of the portable casing 30 and the light generating unit 40 adjacent to the internal lining and internal blood vasculature of a subject's nasal cavity in the manner shown by FIG. 5. In addition, the interchangeability of the applicator that houses the light generator unit allows for different users in a family to have their personal applicators (for hygiene reasons) and to share a single controller and thus save the cost of having separate controllers.

Nevertheless, the applicator 20 shown by FIGS. 3-5 and 8 respectively is deemed to be only one preferred exemplary instance and tangible means for supporting and properly placing the configured irradiation lens 50 within a nostril; and represents only one kind of support construct which makes the in-vivo placement of the configured irradiation lens 50 within a nostril easier, faster and simpler.

III. The Essential Components of the Apparatus

Accordingly, as revealed by the description presented above, it is clear that the non-invasive apparatus of the present invention has only four essential component parts. These are: (i) a portable hollow casing, which also serves as a reflective lens; (ii) a discrete light generating unit which is housed and contained within the interior spatial volume of the hollow casing; (iii) an identifiable source of electrical current; and (iv) a processing and power controller assembly. These four requisite components are electrically linked together by: at least one connector in electrical communication with the source of electrical current for on-demand transfer of direct electrical current to the controller assembly; and at least one connector in electrical communication with the controller assembly and the light generating unit for on-demand conveyance of direct electrical current from the controller assembly.

Particulars of the structural details and attributes for each of the four essential component parts are illustrated by FIGS. 6-10 respectively; and a more detailed description of each requisite component part is presented below.

1. A Portable Hollow Casing

Each embodiment of the instant invention will include a portable hollow casing having fixed dimensions; a sized internal spatial volume; and an external surface configuration suitable for in-vivo insertion into the nasal cavity space of a nostril, without causing substantial impairment to the subject's ability to breathe.

Typically, the portable casing will be constructed and formed of a light transmitting material over at least a portion of its external surface, and will encompass that volumetric zone intended for housing and containment of at least one light generating unit. By definition, such light transmitting material includes and encompasses transparent, translucent and opaque matter. However, in most instances, a completely clear and transparent matter is deemed best for use.

It is also important to note that the intended purposes and goals of the portable casing are twofold: (1) to serve as a containment chamber that is configured for easy in-vivo insertion into the nasal cavity space of a nostril; and (2) to act as a molded lens that reflects and directs emitted light waves and particles into the deeper regions of the nasal cavity walls for irradiation of the circulating blood. Consequently, the portable hollow casing must have dimensions which are small enough to allow insertion into one nostril; and will minimize impairment of the subject's ability to breathe; and yet will be able to maximize the scattering of the light particles towards the walls of the subject's nasal cavity.

For these reasons, it is very desirable that the hollow casing be fashioned in size and configuration for support by a tangible holder or fixture which the human subject can hold with his fingers. Thus, while the portable casing can be fashioned into any generally slender and elongated shape such as a tubular, or cigar-shaped, or cylindrical format—it is deemed both useful and appropriate that the overall configuration of the portable hollow casing also provide a structural means for support which allows its placement into a nasal cavity space at will. For this reason, the "L" shaped format illustrated by FIG. 7 is very desirable and is considered to be an optimal configuration.

2. The Light Generating Unit(s)

Each light generating unit is capable of generating light energy of at least one preselected wavelength on-demand. It is intended that the light generating unit will be able to deliver therapeutic light at wavelengths that include the following: In the visible color spectral ranges—the red, green and/or blue light wavelengths; and in the non-visible spectral ranges—the infrared, near-infrared and ultraviolet light wavelengths.

In addition, the generated light energy waves and particles may alternatively be either coherent (as in lasers) or incoherent; be either pulsed or non-pulsed in delivery; be either constant or non-constant in intensity; be either uniform or non-uniform in phase; polarized and non-polarized; and have a regular or irregular flux.

Clearly, any conventionally known means for generating electromagnetic radiation or articles for propagating radiant energy are acceptable for use in the present apparatus; and in the majority of embodiments, it is intended and expected that either a low level laser unit or a light emitting diode (LED) will be employed as the light generating unit(s) for irradiating the blood.

Accordingly, the apparatus requires only a functional light generating unit or units; and it is of no consequence to the present invention what the nature, or construction, or format of the light generating unit might be so long as it generates and transmits light of at least one pre-chosen wavelength.

Potentially Useful Light Wavelengths

The visible light spectrum corresponds to a wavelength range between 400-700 nanometers (nm) and provides a color range of violet through red. The visible colors from shortest to longest wavelength are: violet, blue, green, yellow, orange, and red. In comparison, ultraviolet radiation has a shorter wavelength than the visible violet light; and infrared radiation has a longer wavelength than visible red light. Also, white light is a mixture of the colors of the visible spectrum; while black light is a total absence of light.

Figure 11:
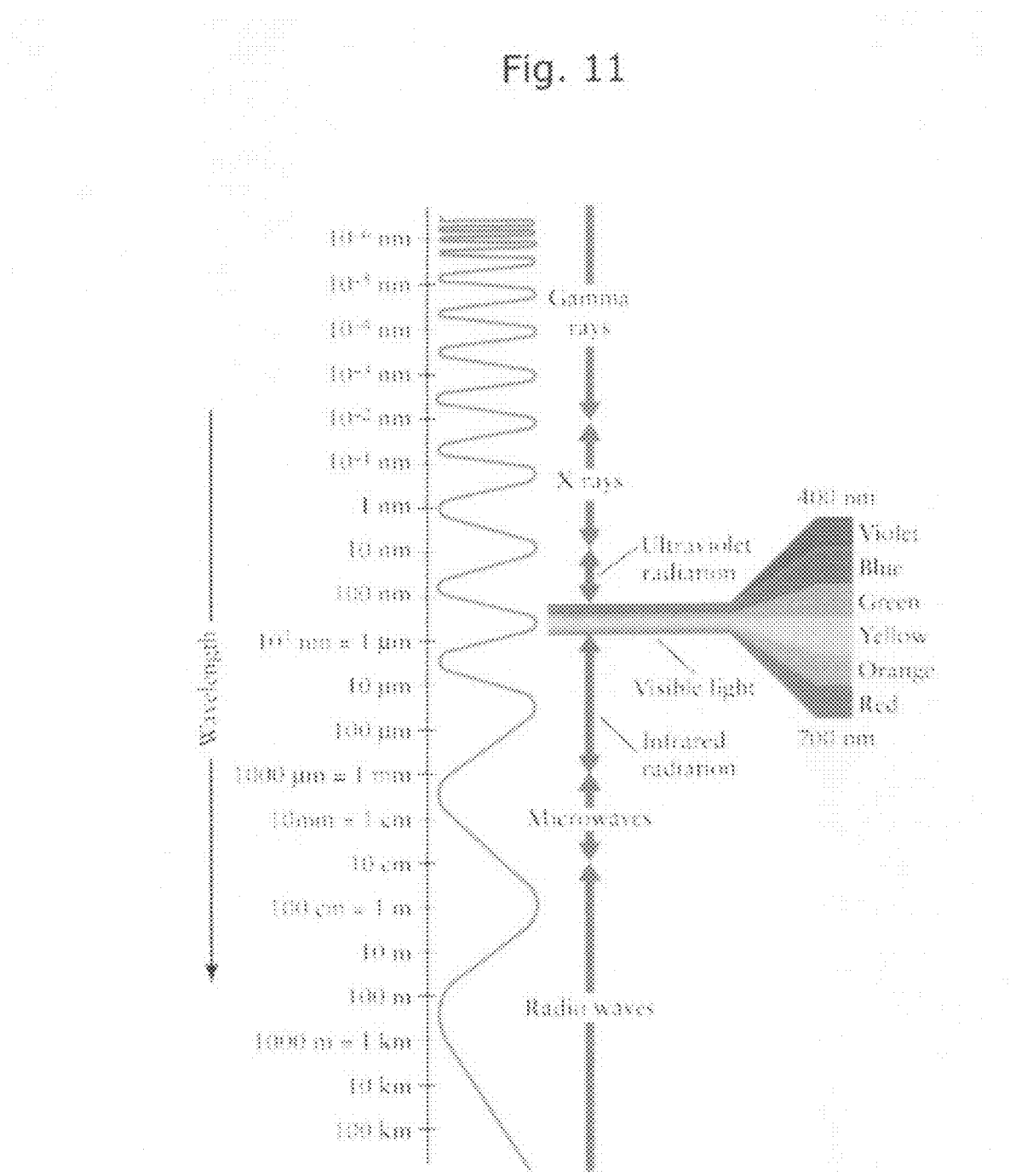
FIG. 11 is an illustration showing the full range of light energy wavelengths.
Figure 12:
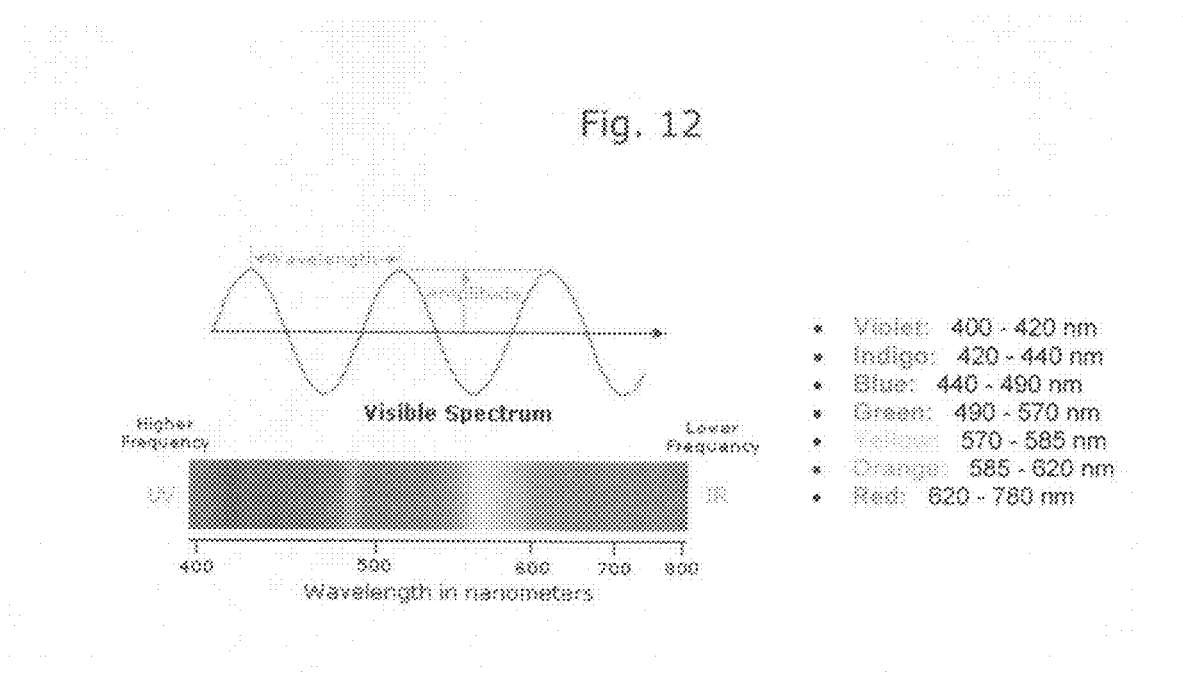
FIG. 12 is an illustration of visible light energy wavelengths.

For completeness, the entire spectrum of visible and invisible light wavelengths that can be provided by one or more of the light generating unit(s) is illustrated by Table 1 below and FIGS. 11 and 12 respectively.

TABLE 1

| Visible Color Wavelength Ranges | |
| --- | --- |
| Violet: | 400-420 nm |
| Indigo: | 420-440 nm |
| Blue: | 440-490 nm |
| Green: | 490-570 nm |
| Yellow: | 570-585 nm |
| Orange: | 585-620 nm |
| Red: | 620-780 nm |

Therapeutically Effective Light Ranges and Wavelengths

A guiding principle of the invention is to transmit and deliver a therapeutically efficacious energy dosage to the blood capillary bed in the living tissues forming the nasal cavity. For this purpose, it is generally preferred that at least coherent visible red light generated by a low level laser, or incoherent visible red light generated by a light emitting diode, and is fixed at wavelengths ranging between 620-780 nm be used. These light generating units are set at a 655 nm wavelength for the preferred low level laser embodiment and at 630 nm for the LED embodiment; will operate well and effectively; and will cause the disaggregation of RBC clusters in-vivo within the blood capillary beds of the nostril.

For these reasons, various preferred embodiments of the apparatus and system will transmit and direct either coherent or incoherent visible light energy at red color wavelengths ranging between 620-780 nm, with a radiant power between 1-10 mW. In comparison, some embodiments of the irradiation apparatus and system will emit and deliver visible light energy at wavelengths of between 495-570 nm with a radiant power of 1-10 mW (the green color range); and, in the alternative, still other embodiments will emit visible light energy at wavelengths ranging between 450-495 nm (the blue color range) at a radiant power between 1-10 mW.

In addition, another class of embodiments of the irradiation apparatus and system will employ and utilize non-visible light wavelengths for achieving therapeutic irradiation effects in-vivo. In these instances, some of these embodiments will generate coherent (laser) near-infrared light at wavelengths between 700-1400 nm; while other non-visible embodiments will transmit non-coherent near-infrared light at wavelength between 700-1400 nm; and still other embodiments will generate and utilize a combination of two or more of these non-visible light ranges (the infrared, near-infrared and ultraviolet light wavelengths).

3. A Source of Electric Current

It is required that a portable and replenishable source of on-demand direct electrical current exist as a component part of the apparatus and system of the present invention. The therapeutic treatment provided by the instant invention is intended to be delivered at a specific energy dosage (measured in joules), which is a function of power (in wattage) and time (in seconds) that is deemed to be efficacious for each therapeutic treatment.

In the preferred embodiment shown by FIGS. 3 and 4, a 1.5 volt dry cell battery is employed to power the laser diode—which in turn delivers an energy dosage of about 7 joules of light energy at a 655 nm wavelength for transmission into the tissue walls of the nasal cavity for irradiation of the superficially disposed blood capillary beds. In these use instances and conditions, effective therapeutic results (disaggregation of RBC clusters in the circulating blood) can obtained in a very short time—i.e., after only 25 minutes' treatment time. In other embodiments, 'an alternative light source would require a different configuration of power, energy dosage and treatment time.

The power supply typically will convey energy in the form of direct electric current; and adequate quantities of electric current can be repeatedly conveyed from either from a single battery source or from a combination of several dry cells joined together in series or parallel. In some other desirable embodiments, the source of electric power will be in the form of a rechargeable direct current battery unit (rechargeable from ordinary household alternating current receptacles) or alternating current (AC) via a power adaptor.

As to positioning, in all preferred embodiments, the power source is a discrete entity which is held and contained entirely within the internal confines of the controller assembly 80. In less preferred embodiments, however, the source of electric current can be a self-contained, separate and free standing unit which is in electric communication with the controller assembly via an electrical cable and connector module linkage.

4. A Process Controller Assembly

Figure 10:
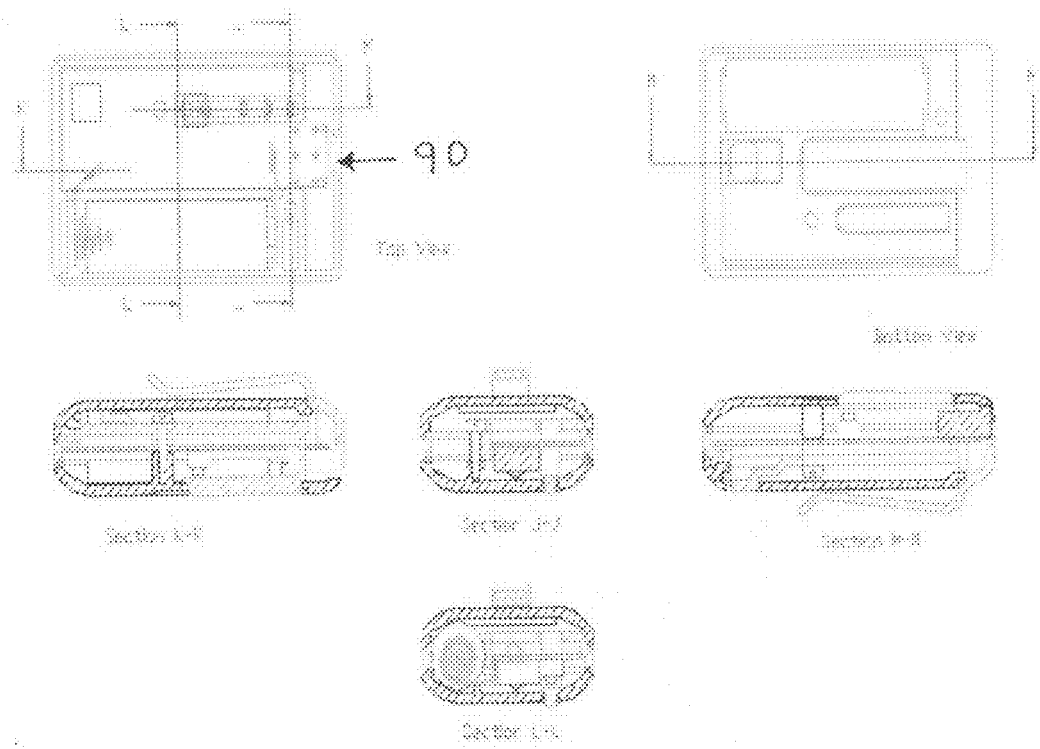
FIG. 10 is a collection of illustrations showing multiple cross-sections views of the process controller assembly in the preferred apparatus as seen in FIG. 3.

The process controller assembly is a portable unit component having three structural features. Thus, as illustrated by FIGS. 9 and 10 respectively, each process controller assembly will include:

(i) A receiving circuit for receipt of such direct electrical current as is transferred to the controller assembly from the electric source.

(ii) A central processing unit (CPU) for controlling and directing the flow of such electrical current as is received by the controller assembly over time.

(iii) A delivery circuit for delivering direct electrical current from the controller assembly to another component.

Equally important, it is intended and expected that the process controller assembly will be electrically linked to the other essential components of the apparatus and thus typically will also have (α) At least one connector in electrical communication with the source of electrical current for on-demand transfer of electric current to the controller assembly; and (β) At least one connector in electrical communication with the light generating unit for on-demand conveyance of electric current from the controller assembly to the light generating unit(s).

These connectors typically are formed as insulated copper wire cables and jack modules that allow for quick and easy linkage and electrical communication with both the power source and the light generating unit(s).

In all embodiments of the apparatus, the process controller assembly will not operate in the absence of a source of electric current. In addition, the controller assembly, besides switching off the unit after a predetermined time, is mainly a circuitry which provides power to drive the light generating unit properly and efficiently. The controller also ensures that the power delivered to the light generating unit is consistent. It therefore desirably monitors the battery strength, and switches off the unit if the battery if it is unable to supply sufficient power to drive the circuitry properly.

Accordingly, as shown by FIGS. 3-4 and 9-10 respectively, the preferred process controller assembly 80 is small in size, light in weight, and portable; preferably has fixed dimensions which are no larger than an average shirt pocket—i.e., approximately 4.5 inches in length, by 4.5 inches in width, by 1 inch in depth; and is formed of a resilient material such as a moldable thermoplastic. Preferred embodiments of the controller assembly typically include a central processing unit (CPU) 100 which is able to control and direct the flow of electric current in dosage, power, and time from the power source to the configured irradiation lens 50.

Note also that in the preferred embodiment shown by FIGS. 3 and 4, the source of direct electric current lies internally and is contained within the interior spatial volume of the controller assembly; and appears as the electric battery 90 (dry cell or rechargeable unit). In this instance, the controller assembly 80 also has a socket adapted for the attachment of an insulated copper wire cable and modular jack connector 70, whose other end is joined to the light generating unit 40 disposed within the hollow casing 30.

The controller assembly 80 illustrated by FIGS. 9-10 as a whole is able to deliver the required dosage from the light diode repeatedly over time, which is sufficient to achieve consistent results of erythrocyte disaggregation and reduced blood viscosity in-vivo. Also, for portability, a typical battery source of electric energy provides direct current at 1.5 volts. However, subject to the circuit to the type of light source being used, a broader range of direct current voltages is acceptable.

The CPU of the controller assembly is able to regulate light energy power output at 5-10 mW. When it is regulated, the power is typically fixed. Thus, in the low level laser embodiment, it is typically 5 mW; whereas in the LED embodiments, it is typically 8 mW. These light energy power outputs result in the emitted light of the apparatus being therapeutically effective after a treatment time of only 25 minutes duration for the preferred embodiments.

It is intended and expected that any conventionally known and interchangeable electric cables and connectors will be used to link the controller assembly to the irradiation lens. This also provides a distinct advantage and benefit to the user—i.e., the option to exchange one configured irradiation lens (able to transmit light at a first wavelength) for another irradiation lens (able to transmit light at a second and different wavelength); and thereby permits the use of different lasers and alternative light emitting diodes able to deliver different wavelengths of visible and invisible light energy with one single controller assembly.

This particular advantage and benefit is provided through the selection of various pre-configured settings on the controller to match the type of light and its wavelength. This mode and manner of exchanging the light generating units at will or as needed allows the therapeutic use of different light ranges and alternative light wavelengths by a single patient without any need for purchasing multiple treatment systems or more than one apparatus.

III. Notable Features and Capabilities of the Apparatus as a Whole

The apparatus provides a number of unique attributes, properties, and capabilities. Among them are the following:

1. The apparatus and system can deliver light energy over a variety of selected wavelengths to achieve disaggregation of RBCs in the blood 2. The apparatus and system have very low electric power requirements.

3. The apparatus and system provide an easy to use applicator which can be clipped to the external wall of a nostril while concomitantly inserting an encased solid state electronic light source (such as the light emitting diode or a low level laser unit) within the nasal cavity to deliver the light therapy.

4. The apparatus and system overcome the disadvantages of the prior art and the limitations of conventional technologies, particularly with regards to portability and self-administration. It also markedly differs from known system as to the method by which light therapy is delivered to the capillary beds adjacent the walls of the nasal cavity.

5. The apparatus and system is able to illuminate the blood rich inner walls of the nasal cavity where a bed of vascular capillaries lies just beneath the surface. In this respect, the wavelengths of light are pre-selected so as to achieve disaggregation of the red blood cells and lower the viscosity of the blood in the body. This results in improved rheological properties for the blood system, and in altered blood and plasma components' properties.

6. The apparatus and system will direct dispersed light waves and particles and achieve wide light coverage of the interior nasal cavity walls, with minimum leakage through the anterior nasal region.

7. The apparatus and system separate the delivery of light energy from the processing and power controller assembly for both hygiene and cost saving purposes; and also potentially provides for the interchange and substitution of different light generating units with a single processing controller assembly that will convey the appropriate power dosage for this purpose.

IV. The Method of Therapeutic Treatment

The method for performing non-invasive irradiation light therapy within a nasal cavity of a living mammalian subject, said non-invasive therapy method comprises the following acts:

Step 1: obtaining an apparatus comprised of
a configured irradiation lens comprising
a portable hollow casing having fixed dimensions, a sized internal spatial volume, and an external surface configuration suitable for in-vivo insertion into the nasal cavity space of a nostril without causing substantial impairment to the subject's ability to breathe, said portable casing being comprised of
(i) a light transmitting material which forms at least a portion of the external surface for said casing,
(ii) at least one light generating unit disposed within said internal spatial volume of said casing and which is capable of emitting light energy on-demand of at least one preselected wavelength;
portable means for supporting said configured irradiation lens and for at will placement of a light transmitting external surface of said configured irradiation lens within a nostril at a position adjacent to the internal lining and internal blood vasculature of a subject's nasal cavity;
a portable controller assembly including
($\alpha$) a portable and replenishable power source of on-demand direct electrical current,
($\beta$) a central processing unit for controlling and directing the flow of such direct electrical current, and
($\gamma$) at least one connector in electrical communication with said configured irradiation lens for on-demand conveyance of direct electrical current from said controller assembly to said light generating unit;

Step 2: Placing a transparent external surface of said configured irradiation lens within a nostril at a position adjacent to the internal lining and internal blood vasculature of a subject's nasal cavity; and Step 3: Causing said light generating unit of said positioned configured irradiation lens to generate light energy of at least one preselected wavelength upon the internal lining and internal blood vasculature of a subject's nasal cavity for a predetermined amount of time.

Figure 15:
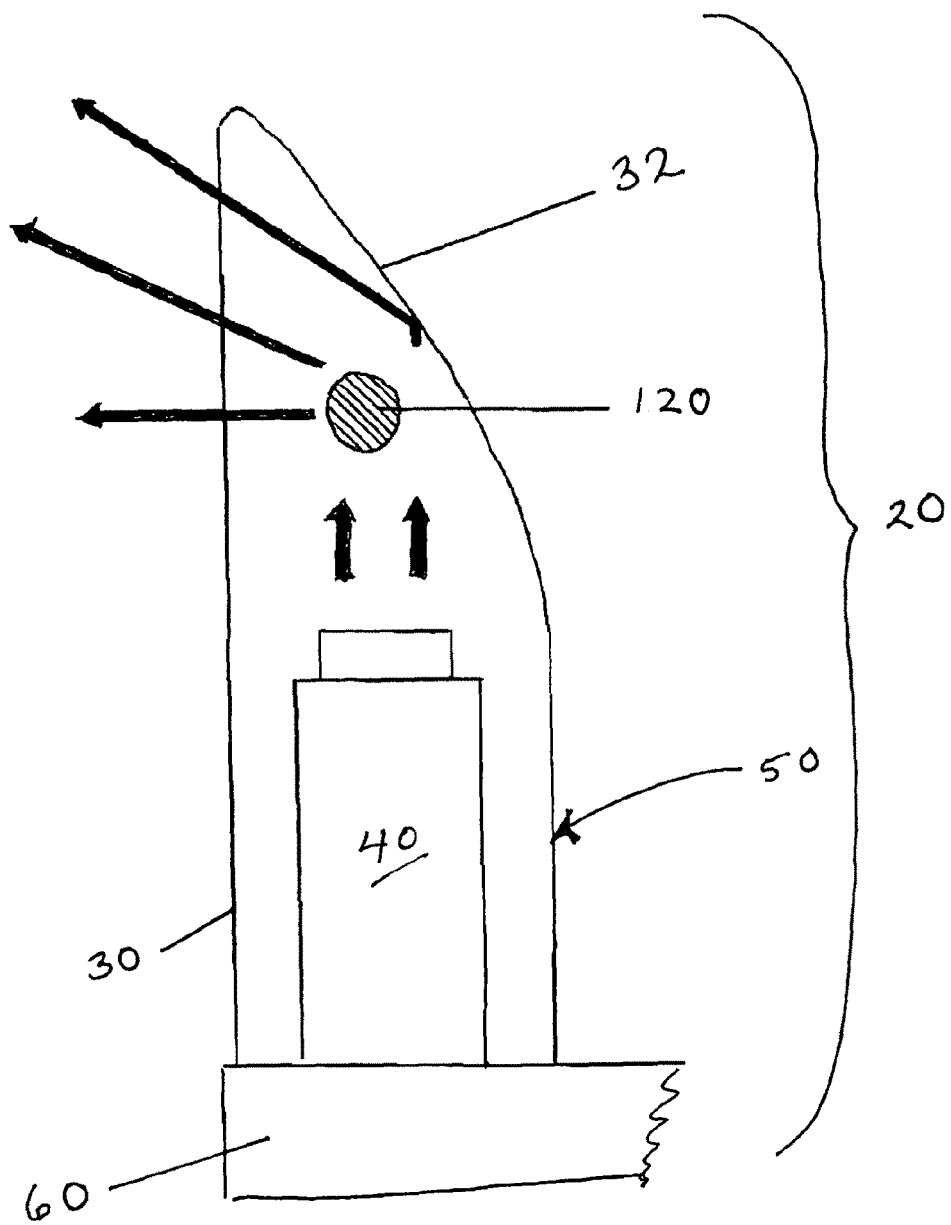
FIG. 15 is a greatly magnified cross-sectional view of the irradiating lens held by the applicator as seen in FIG. 13.

The treatment methodology as recited above is illustrated by FIGS. 13-15 respectively. As seen in FIG. 13, one properly inserts the configured irradiation lens 50 using the applicator 20 into the nasal cavity space 220 of the human nose; and then causes direct electric current to be conveyed from its source to the process controller assembly (not shown) and then to the light unit(s) 40 disposed within the hollow casing 30. This will cause the light unit 40 to generate and transmit light waves and particles 150 of a pre-chosen wavelength.

In the preferred laser light embodiments, the transmitted light waves and particles 150 are directed and deflected by the casing wall 32 and the optionally present spherical micro-lens 120 disposed next to the end tip of the light generating unit 40 within the hollow casing 30. This is illustrated best by FIGS. 14 and 15 respectively.

By this process, the light waves and particles 150 emanating from the configured irradiating lens 50 become focused, aimed, and directed towards the deeper regions of the tissues forming the nasal cavity walls 200, where the rich vascular capillaries beds lie. The aimed light energy from the light generating unit 40 is largely deflected towards the internal section of the nasal cavity; and such light as might pass through the entire thickness of the nostril wall 200 then is reflected and redirected back into the nasal cavity space by the reflective white opaque material of the nose clip 64. Thus, as shown by FIG. 14, most of the initially generated light is captured and aimed (by deflection and reflection) into the interior walls 200 of the nasal cavity.

In the preferred embodiment, the process and power controller assembly as a whole is able to deliver a dosage of about 7 joules, which is sufficient to achieve consistent results of erythrocyte disaggregation and reduced blood viscosity in-vivo. Also, the battery source of electric energy within the controller assembly provides direct current at a constant 1.5 volts and the CPU of the controller assembly is able to regulate light energy power output consistently at 5-10 mW. This results in the emitted light of the apparatus being therapeutically effective after a treatment time of only 25 minutes duration.

V. An In-Vivo Clinical Study and its Results

A clinical study using human volunteers as subjects was conducted to determine the aggregation state of red blood cells before and after a 25 minute treatment using the apparatus and system of the present invention. A complete description and full details of this study and the obtained results are presented below.

It will be recognized that no attempt was made to make any medical diagnosis over the course of this clinical study. Instead, the true purpose of this in-vivo experiment is the collection of empirical blood data and to document the therapeutic effect of the apparatus and treatment methodology on the state of aggregation of the red blood cells then circulating in that patient's blood. Also, although the effect on blood viscosity was not measured in these tests, medical personnel were able to visually observe the viscosity of patient blood as the blood samples were extracted from the test subject.

Methodology

The clinical study was conducted over a 22 months' time period and involved a total of 348 human subjects.

All the human subjects voluntarily agreed to have their blood taken, analyzed, and treated with the apparatus described in detail above and illustrated by FIGS. 3 and 4. Before each treatment, every subject had his or her finger tip pricked with a lancing device to extract a small sample of blood. This blood sample was placed on a glass slide and observed under a microscope magnified 400x. Using video capture software, a 4 second video image was captured and recorded into a computer hard disk.

The patient pool was made up of random volunteers, aged between 9 and 85 years. No preliminary medical history was recorded, and no person was excluded. Each subject only underwent one treatment which was recorded. The blood analyses and evaluations were supervised by a trained and experienced technician. The tests were conducted in various places and were self-funded.

The subject then attached the applicator of the apparatus to his nose, and inserted the configured irradiation lens into his nasal cavity. After the light generating unit in the configured irradiation lens is in position, each subject himself turned on the timer and power switch of the controller assembly. The timer automatically turned itself off after 25 minutes treatment. Immediately thereafter, another sample of his blood was carefully extracted, again observed under the microscope, and then recorded on video capture software.

Summary of Empirical Data and Results

| 1. Initial differences | |
|---|---|
| The total number of human subjects in the study = | 348 |
| The total number of human subjects whose blood initially showed aggregated RBCs = | 297 |
| The total number of human subjects whose blood initially showed disaggregated RBC = | 51 |
| Of those human subjects whose blood initially showed aggregated RBCs: Results after irradiation treatment | |
| Significant disaggregation = | 271 persons (91.3%) |
| No significant change observed = | 23 persons (7.7%) |
| Aggregation appearing worse = | 3 persons (1%) |
| Of those human subjects whose blood initially showed disaggregated RBCs: Results after irradiation treatment | |
| No significant change observed = | 43 persons (84.3%) |
| Aggregation appearing = | 8 persons (15.7%) |
| 2. Empirical data analyzed by gender Male Data | |
| Total number of male subjects = | 141 males |
| Number of male subjects whose blood initially showed aggregated RBC = | 122 males |
| Number of male subjects whose blood initially showed disaggregated RBC = | 19 males |
| Of those male subjects that started with aggregated RBCs: Results after irradiation treatment | |
| Significant disaggregation = | 111 males (91%) |
| No significant change observed = | 10 males (8.2%) |
| Aggregation appearing worse = | 1 male (0.8%) |
| Of those male subjects that started with disaggregation RBCs: Results after irradiation application | |
| No significant change observed = | 16 males (84.2%) |
| Aggregation appearing = | 3 males (15.8%) |
| Female Data | |
| Total number of female subjects = | 207 female |
| Number of female subjects whose blood initially showed aggregated RBCs = | 175 females |
| Number of female subjects whose blood initially showed disaggregated RBCs = | 32 females b |
| Of those female subjects whose blood initially showed aggregated RBCs: Results after irradiation application | |
| Significant disaggregation = | 160 females (91.4%) |
| No significant change observed = | 13 females (7.4%) |
| Aggregation appearing worse = | 2 females (1.2%) |
| Of those female subjects whose blood initially showed disaggregated RBCs: Results after irradiation application | |
| No significant change observed = | 27 females (84.4%) |
| Aggregation appearing = | 5 females (15.6%) |

3. Conclusions

1. Via these empirical data and observations, the apparatus and therapeutic method of the present invention markedly reverses the aggregation of RBCs in vivo with merely a single treatment. This is supported in 91 percent of the human test instances when some observed form or degree of RBC aggregation is initially present. Nevertheless, even in that approximately 8 percent of the human test instances where no meaningful change was observed immediately after the 25-minute therapeutic treatment session, it is important to note that the blood samples of these human subjects did in fact exhibit RBC disaggregation when a second blood sample was taken again following a further waiting time of at least another 5 minutes.

Therefore, one can say with full confidence that RBC disaggregation is in fact achieved in 99 percent of the human test cases where the patient's blood initially showed the existence of some RBC aggregation. Only in one percent of the test cases did find a contrary result.

2. The empirical results revealed that the therapeutic effects of the treatment method are very similar between male and female subjects. This result and outcome shows that there is statistical consistency among humans without any gender bias.

3. The viscosity of the human blood samples also appear to be lower after irradiation treatment. This is observation was noted and recorded when the blood sample is extracted after the irradiation treatment session.

The present invention is not restricted in form nor limited in scope except by the appended claims.

What we claim is:

1. A dedicated apparatus for performing non-invasive irradiation light therapy upon the blood then circulating in-vivo within the internal vasculature of a nasal cavity of a living mammalian subject, said non-invasive dedicated apparatus comprising:
    a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing being comprised of
        (i) a light transmitting material which forms at least a portion of the configured external surface for said hollow casing,
        (ii) at least one light generating unit entirely housed and contained within said internal spatial volume of said hollow casing and which is capable of generating light energy of at least one preselected wavelength, energy intensity, and duration on-demand sufficient to achieve a reversal of red blood cell aggregation upon the blood then circulating in-vivo within the vasculature of the nasal tissues, and
    wherein said light transmitting material and said light generating unit collectively form a configured irradiation lens which can emit light energy in a desired irradiation direction on-demand after in-vivo insertion of said hollow casing within a subject's nasal cavity; wherein the irradiation can be applied to a region which lies posterior and/or anterior to the limen nasi of the nasal cavity;
    self-administrable applicator means for at will attachment and detachment in-vivo of said light transmitting external surface and said light generating unit of said configured irradiation lens at a fixed position and desired irradiation direction adjacent to the internal lining and internal blood vasculature of a subject's nasal cavity such that a reversal of red blood cell aggregation can be achieved on-demand by irradiation of the blood then circulating in-vivo within the vasculature of a subject's nasal tissues;
    a portable and replenishable power source of on-demand direct electrical current;
    a portable controller assembly able to control on-demand delivery of light energy from said configured irradiation lens after placement of said hollow casing adjacent to the vasculature of a subject's nasal tissues, said controller assembly including
        ($\alpha$) a receiving circuit for receipt of such direct electrical current as is transferred to said controller from said power source,
        ($\beta$) a central processing unit for controlling and directing the flow of such direct electrical current as is received, and
        ($\gamma$) a conveying circuit for conveying direct electrical current from said controller assembly to said light generating unit;
    at least one connector in electrical communication with said source of electrical current for on-demand transfer of direct electrical current to said controller assembly; and
    at least one connector in electrical communication with said controller assembly and said light generating unit housed within said hollow casing for on-demand conveyance of direct electrical current from said controller assembly.

2. The apparatus as recited in claim 1 further comprising a micro-lens housed within said hollow casing.

3. The apparatus as recited in claim 1 wherein said light generating unit disposed within said internal spatial volume of said hollowing casing is a one selected from the group consisting of a laser unit and a non-laser unit.

4. The apparatus as recited in claim 1 wherein said light generating unit disposed within said internal spatial volume of said hollowing casing is a light emitting diode unit.

5. The apparatus as recited in claim 1 wherein the apparatus is self-administered routinely and repetitiously by the patient for therapeutic treatment.

6. The apparatus as recited in claim 1 wherein said light generating unit can generate light energy at any desired medically effective wavelength, energy intensity, and duration.

7. The apparatus as recited in claim 1 wherein said light generating unit can generate light energy chosen from the group consisting of the visible, near-infrared, and infrared light ranges.

8. The apparatus as recited in claim 1 wherein said controller assembly regulates the power to about 5-10 mW.

9. The apparatus as recited in claim 1 wherein said power source of on-demand direct electrical current is 1.5 volt battery.

10. The apparatus as recited in claim 1 further comprising an applicator which can be clipped to the external wall of a nostril while concomitantly inserting said configured irradiation lens within the nasal cavity to deliver the light energy.

11. A non-invasive system for performing irradiation light therapy within a nasal cavity of a living mammalian subject upon the blood then circulating in-vivo within the vasculature of a subject's nasal tissues, said non-invasive system comprising:
    a configured irradiation lens including
        a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing being comprised of
            (i) a light transmitting material which forms at least a, portion of the configured external surface for said hollow casing,
            (ii) at least one light generating unit entirely housed and contained within said internal spatial volume of said hollow casing and which is capable of generating light energy of at least one preselected wavelength, energy intensity, and duration on-demand sufficient to achieve a reversal of red blood cell aggregation upon the blood then circulating in-vivo within the vasculature of the nasal tissues; wherein the irradiation can be applied to a region which lies posterior and/or anterior to the limen nasi of the nasal cavity;
    self-administrable applicator means adapted for support of said configured irradiation lens and for at will placement of said light transmitting external surface of said configured irradiation lens at a fixed position and desired irradiation direction adjacent to the internal lining and internal blood vasculature of a subject's nasal cavity; and
    a portable controller assembly able to control on-demand delivery of light energy from said configured irradiation lens after placement into a subject's nasal cavity such that the blood then circulating in-vivo within the vasculature of a subject's nasal tissues is irradiated, said controller assembly including
- (α) a portable and replenishable power source of on-demand direct electrical current,
- (β) a central processing unit for controlling and directing the flow of such direct electrical current, and
- (γ) at least one connector in electrical communication with said configured irradiation lens for on-demand conveyance of direct electrical current from said controller assembly to said light generating unit.

12. The non-invasive system as recited in claim 11 further comprising at least one power switch which engages and disengages the transfer of direct electrical current from said controller assembly to said configured irradiation lens.

13. The non-invasive system as recited in claim 11 further comprising at least one timer which limits the transfer of direct electrical current from said controller assembly to said configured irradiation lens to a pre-chosen time period.

14. A method for performing non-invasive irradiation light therapy within a nasal cavity of a living mammalian subject upon the blood then circulating in-vivo within the vasculature of a subject's nasal tissues, said non-invasive therapy method comprising the steps of:

obtaining an apparatus comprised of
  a configured irradiation lens including
    a portable hollow casing having fixed dimensions, a sized internal spatial volume, and an external surface configuration suitable for in-vivo insertion into the nasal cavity space of a nostril without causing substantial impairment to the subject's ability to breathe and without invading the nasal tissues of the living subject, said portable casing being comprised of
      (i) a light transmitting material which forms at least a portion of the configured external surface for said hollow casing,
      (ii) at least one light generating unit entirely housed and contained within said internal spatial volume of said hollow casing and which is capable of generating light energy of at least one preselected wavelength, energy intensity and duration on-demand sufficient to achieve a reversal of red blood cell aggregation upon the blood then circulating in-vivo within the vasculature of the nasal tissues,
    whereby said configured irradiation lens can emit light enemy of a preselected wavelength in a desired direction after in-vivo insertion within a nasal cavity and achieve a reversal of red blood cell aggregation on-demand for the blood then circulating in-vivo within the vasculature of a subject's nasal tissues; wherein the irradiation can be applied to a region which lies posterior and/or anterior to the limen nasi of the nasal cavity;
  self-administrable applicator means adapted for support of said configured irradiation lens and for at will placement of said light transmitting external surface of said configured irradiation lens at a fixed position and desired irradiation direction within a nostril adjacent to the internal lining and internal blood vasculature of a subject's nasal cavity;
  a portable controller assembly able to control on-demand delivery of light energy from said configured irradiation lens to the vasculature of a subject's nasal tissues, said controller assembly including
    (α) a portable and replenishable power source of on-demand direct electrical current,
    (β) a central processing unit for controlling and directing the flow of such direct electrical current, and
    (γ) at least one connector in electrical communication with said configured irradiation lens for on-demand conveyance of direct electrical current from said controller assembly to said light generating unit;
placing a transparent external surface of said configured irradiation lens within a nostril at a desired fixed position adjacent to the internal lining and internal blood vasculature of a subject's nasal cavity; and
causing said light generating unit of said positioned configured irradiation lens to generate light energy of at least one preselected wavelength, energy intensity and duration upon the internal lining and internal blood vasculature of a subject's nasal cavity for a predetermined amount of time such that a reversal of red blood cell aggregation is achieved for the blood then circulating in-vivo within the vasculature of a subject's nasal tissues.

15. The method as recited in claim 14 wherein light energy is caused to be delivered over a variety of selected wavelengths to achieve disaggregation of RBCs in the blood.

16. The method as recited in claim 14 wherein said generation of light has low electric power requirements.

17. The method as recited in claim 14 wherein the inner walls of the nasal cavity and the vascular capillaries which lie beneath the surface of said inner walls are illuminated by said generated light.

18. The method as recited in claim 14 wherein the wavelengths of generated light are pre-selected to achieve disaggregation of red blood cell clusters.

19. The method as recited in claim 14 wherein the wavelengths of generated light are pre-selected to achieve a lowering of the viscosity of the blood circulating within the body.

* * * * *